United States Patent [19]

Yamaguchi et al.

[11] 3,943,239

[45] Mar. 9, 1976

[54] STABILIZED INSECTICIDAL COMPOSITION

[75] Inventors: Takashi Yamaguchi, Takarazuka; Yasuo Abe, Nishinomiya; Yoshio Fujita, Kobe; all of Japan

[73] Assignees: Sumitomo Chemical Co., Ltd.; Dai-Nippon Jachugiku Co., Ltd., both of Osaka, Japan

[22] Filed: May 28, 1974

[21] Appl. No.: 473,474

[30] Foreign Application Priority Data

May 25, 1973 Japan................................ 48-58980

[52] U.S. Cl. ...................... 424/43; 424/27; 424/40; 424/45; 424/174; 424/285; 424/340; 424/346
[51] Int. Cl.² ..................... A01N 9/28; A01N 17/02
[58] Field of Search .......... 424/40, 45, 174, 285, 43

[56] References Cited
UNITED STATES PATENTS

| | | | |
|---|---|---|---|
| 3,510,558 | 5/1970 | Hamuro.............................. | 424/274 |
| 3,560,613 | 2/1971 | Mistcus et al....................... | 424/174 |
| 3,833,564 | 9/1974 | Martel ............................. | 424/285 X |

OTHER PUBLICATIONS

Ito, Chem. Abst., Vol. 55, 1961, p. 20518b.

Oishi, Chem. Abst., Vol. 55, 1961, p. 21660f.

Chem. Abst., Eighth Coll. Index, Vols. 66–75 (1967–1971), p. 23091s.

*Primary Examiner*—Stanley J. Friedman
*Assistant Examiner*—Allen J. Robinson
*Attorney, Agent, or Firm*—Sughrue, Rothwell, Mion, Zinn & Macpeak

[57] ABSTRACT

A stabilized insecticidal composition having improved stability to light and containing a synthetic pyrethroid insecticide such as chrysanthemum-monocarboxylic acid 5-propargyl-2-furyl methyl ester, chrysanthemum-monocarboxylic acid 2-methyl-5-propargyl-3-furyl methyl ester, chrysanthemum-monocarboxylic acid 5-propargyl-α-ethynyl-2-furyl methyl ester, chrysanthemum-monocarboxylic acid 5-benzyl-3-furyl methyl ester or 2,2-dimethyl-3-(2,2-dichlorovinyl)cyclopropane-1-carboxylic acid 5-benzyl-3-furyl methyl ester, and at least one of 3,5-di-t-butyl-4-hydroxyanisole and 2,2'-methylenebis(6-t-butyl-4-ethylphenol).

2 Claims, No Drawings

STABILIZED INSECTICIDAL COMPOSITION

BACKGROUND OF THE INVENTION

1. Field of the Invention

The present invention relates to a stabilized insecticidal composition, and more particularly it relates to a stabilized composition of chrysanthemum-monocarboxylic acid 5-propargyl-2-furyl methyl ester (hereinafter, designated "Insecticide I"), chrysanthemum-monocarboxylic acid 2-methyl-5-propargyl-3-furyl methyl ester (hereinafter, designated "Insecticide II"), chrysanthemum-monocarboxylic acid 5-propargyl-α-ethynyl-2-furyl methyl ester (hereinafter, designated "Insecticide III"), chrysanthemum-monocarboxylic acid 5-benzyl-3-furyl methyl ester (hereinafter, designated "Insecticide IV"), or 2,2-dimethyl-3-(2,2-dichlorovinyl)cyclopropane-1-carboxylic acid 5-benzyl-3-furyl methyl ester (hereinafter, designated "Insecticide V"), each of which is known as a synthetic pyrethroid insecticide.

2. Description of the Prior Art

The above-described synthetic pyrethroid insecticides have a strong quick insecticidal activity and high safety to humans and animals, and thus they are useful as an effective insecticidal component for aerosols, oils, mosquito sticks or coils (mosquitocides), etc., in mainly domestic and epidemic prevention uses.

However, these insecticides have poor chemical stability, that is, they have the disadvantages that it is difficult to maintain their purity directly after their preparation for a specific period of time as well as after the operations necessary for producing usable insecticidal compositions containing these compounds as an active ingredient, such as, for example, mixing with water, various organic solvents, animal powders, plant powders, or mineral powders and heating. They are easily decomposed by the action of light, air, etc., with their activity being diminished and coloration occurring.

It is known and generally practiced to add 2,6-di-t-butyl-4-methylphenol (hereinafter, designated Additive C), 2-t-butyl-4-methoxyphenol (hereinafter, designated Additive D), etc., to the above-described insecticide to stabilize the insecticide but as will be shown hereinafter in the examples of this invention, the effect of such conventional additives is not always sufficient nor is the purpose for use satisfied as the case may be.

SUMMARY OF THE INVENTION

As the results of various investigations for effectively stabilizing these insecticides, it has been discovered that by adding to the insecticide at least one of 3,5-di-t-butyl-4-hydroxyanisole (hereinafter, designated "Additive A") and 2,2'-methylenebis(6-t-butyl-4-ethylphenol) (hereinafter, designated "Additive B"), the change in the properties of the insecticide with the passage of time as described above can be completely prevented for a long period of time and at the same time coloration can be also prevented completely.

Therefore, an object of this invention is to provide an effectively stabilized synthetic pyrethroid insecticide insecticidal composition.

Another object of this invention is to provide a stabilized synthetic pyrethroid insecticide insecticidal composition which retains its purity and insecticidal activity for a long period of time without discoloration.

Still another object of this invention is to provide an additive for stabilizing quite effectively synthetic pyrethroid insecticides.

Thus, the present invention provides a stabilized insecticidal composition comprising a synthetic pyrethroid insecticide, i.e., chrysanthemum-monocarboxylic acid 5-propargyl-2-furyl methyl ester, chrysanthemum-monocarboxylic acid 2-methyl-5-propargyl-3-furyl methyl ester, chrysanthemum-monocarboxylic acid 5-propargyl-α-ethynyl-2-furyl methyl ester, chrysanthemum-monocarboxylic acid 5-benzyl-3-furyl methyl ester, or 2,2-dimethyl-3-(2,2-dichlorovinyl)cyclopropane-1-carboxylic acid 5-benzyl-3-furyl methyl ester and at least one of 3,5-di-t-butyl-4-hydroxyanisole and 2,2'-methylenebis(6-t-butyl-4-ethylphenol).

DETAILED DESCRIPTION OF THE INVENTION

Sufficient effects are obtained with insecticidal compositions containing the additive of this invention even under severe conditions where conventional additives do not sufficiently stabilize the insecticides, such as, in particular, when used in an electric anti-mosquito fumigator heated at about 150°C, mosquito sticks or coils, and a retentive spray which is frequently exposed to light and oxygen during suspension. Hence the excellent effects of the additive of this invention gives rise to the presumption that antioxidant or ultraviolet absorbent effects are achieved.

The stabilizers in this invention can be used alone or in combination or, if desired, can be used together with other additives such as antioxidants, ultraviolet absorbents, etc. The proportion of the additive or additives in the stabilized insecticidal composition of this invention ranges from about 0.05 to 3% by weight to the weight of the synthetic pyrethroid insecticide under general use conditions but the proportion thereof is not to be interpreted as being limited to only this range. For example, when the stabilizer is added to the insecticide in the same amount as or twice as large as the amount of the insecticide where the composition is to be used in preparing mosquito sticks or coils or in electric anti-mosquito fumigators, thermal decomposition of the insecticide can be prevented and thus the ability to use the composition as a fumigant can be increased. This shows the insecticidal effects of the composition are further improved by the employment of large amount of the additive.

In the practice of this invention, the stabilized insecticidal composition of this invention can be prepared by mixing the insecticide, the additive or additives of this invention, other additives, and, if desired, those materials necessary for preparing the insecticidal composition in a usable form in any desired order.

The insecticidal compositions of this invention will further be explained in greater detail together with the effects thereof by reference to the following examples although it is to be understood that these examples are not to be interpreted as limiting the scope of this invention. Unless otherwise indicated, all parts, percents, ratios and the like are by weight.

EXAMPLE 1

The insecticidal composition of this invention was prepared by adding 1% by weight of Additive A to Insecticide I. On the other hand, comparison samples were prepared by adding 1% by weight of each of the conventional additives as shown in Table 1 below to Insecticide I. Each of the samples thus prepared was placed in a glass sample tube and the tube was stored open. After a fixed time, the sample was analyzed using gas chromatography to determine the change in properties with the passage of time with respect to a standard sample. The results obtained are shown in Table 1.

TABLE 1

| Test Sample | Additive | Purity (%) of Insecticide I Assuming the Original Purity was 100% | | |
|---|---|---|---|---|
| | | 7 Days | 14 Days | 21 Days |
| Invention | Additive A | 101.1 | 99.4 | 98.9 |
| Comparison Samples | None | 66.3 | 50.5 | 26.7 |
| '' | Additive C | 95.6 | 87.8 | 67.1 |
| '' | Additive D | 87.0 | 73.8 | — |
| '' | Additive E* | 88.9 | 67.9 | — |
| '' | Additive F* | 84.9 | 62.5 | — |

Note:
Additive E*: 1,1-bis(4-Hydroxyphenyl)cyclohexane
Additive F*: 3-Methyl-4-isopropyl-6-t-butylphenol From the above results it is clear that the change in properties of the insecticidal composition of this invention was remarkably less than the change in properties of the comparison samples.

EXAMPLE 2

The insecticidal compositions of this invention were prepared by adding 1% by weight of Additive A to each of Insecticides II, III, IV and V. Each of the compositions prepared was stored at 60°C as described in Example 1 and the change in properties with the passage of time was determined in each case. The results obtained are shown in Table 2 below together with the results of comparison samples prepared by adding conventional Additive C to each of the insecticides.

TABLE 2

| Insecticide | Additive | Purity (%) of Each Insecticide Assuming the Original Purity was 100% | | |
|---|---|---|---|---|
| | | 7 Days | 14 Days | 21 Days |
| II | A | 98.6 | 96.5 | 95.3 |
| II | C | 94.2 | 85.6 | 66.1 |
| III | A | 95.4 | 92.2 | 88.1 |
| III | C | 89.7 | 76.4 | 49.2 |
| IV | A | 99.1 | 98.6 | 97.9 |
| IV | C | 98.5 | 95.1 | 90.1 |
| V | A | 99.5 | 99.2 | 98.1 |
| V | C | 98.7 | 96.1 | 93.4 |

From the above results, it is clear that each of the insecticides was stabilized more effectively using the stabilizer (Additive A) of this invention.

EXAMPLE 3

Insecticidal compositions of this invention were prepared by dissolving 1000 mg of Insecticide I and 30 mg of Additive A or Additive B sufficient in acetone to make the total volume 100 ml. The liquid composition (0.5 ml) thus prepared was applied to a filter paper having a diameter of 7 cm and after removing the acetone, the filter paper was allowed to stand in a room under indirect radiation from the sun. After a fixed time, the composition on the filter paper was extracted with acetone and the change in color of the composition was detected using a Gardner scale. Also, by analyzing the extract using gas chromatography, the remaining percentage of Insecticide I was determined. The results obtained are shown in Table 3 together with the results obtained for comparison samples prepared by adding each of Additives C and D to Insecticide I.

TABLE 3

| Test Sample | Additive | Percent of Insecticide I Remaining | | |
|---|---|---|---|---|
| | | Initial | 2 Days | 4 Days |
| Invention | A | 100 (1) | 50.6 (2) | 32.5 (3) |
| '' | B | 100 (1) | 72.1 (1) | 39.8 (2) |
| Comparison Samples | None | 100 (1) | 19.6 (4) | 0 (6) |
| '' | C | 100 (1) | 22.3 (4) | 0 (6) |
| '' | D | 100 (1) | 20.1 (4) | 0 (6) |

Note:
The figures in the parentheses show the color number on the Gardner scale.

The results of this example show that under the conditions of sufficient exposure to room light and atmospheric oxygen, the composition of this invention was more remarkably stabilized and also the change in color of the composition of this invention was less as compared with the comparison samples.

EXAMPLE 4

An acetone solution (1 ml) containing 70 mg of Insecticide I, 140 mg. of piperonyl butoxide, and 50 mg of Additive A or Additive B was applied to a small piece of pulp to impregnate the pulp with the solution and then the acetone was evaporated off to provide an electric mosquitocidal mat. The mat was heated to 145°C using a hot plate and after a fixed time, the percentage of the insecticide volatilized and the percentage of the insecticide remaining in the mat were measured, whereby the loss of Insecticide I including the loss due to thermal decomposition was determined. Comparison samples were also prepared in the same way as described above using, however, Additive C in place of Additive A or Additive B or without using any additive. The results obtained are all shown in Table 4 below.

TABLE 4

| Test Sample | Additive | Time (Hour) | Percentage Volatilized | Percentage Remaining | Loss (%) |
|---|---|---|---|---|---|
| Invention | A | 4 | 66.0 | 27.4 | 6.6 |
| '' | A | 8 | 75.2 | 18.1 | 6.7 |
| '' | B | 4 | 63.8 | 26.4 | 9.8 |
| '' | B | 8 | 71.9 | 18.2 | 9.9 |
| Comparison Samples | None | 4 | 45.1 | 22.6 | 32.3 |
| '' | '' | 8 | 50.0 | 14.0 | 36.0 |
| '' | C | 4 | 46.5 | 23.9 | 29.6 |
| '' | C | 8 | 53.4 | 16.0 | 30.6 |

As is clear from the results shown in Table 4 above, the percentage of the insecticide remaining in the mat did not differ greatly in both cases but the percentage of the insecticide volatilized was considerably higher in the case of this invention as compared with the comparison samples and the loss of the insecticide was considerably less in this invention than with the comparison samples, which indicates that Insecticide I in the mat was volatilized without being decomposed in the samples of this invention.

EXAMPLE 5

To Insecticide III were added Additive A, B, or C and polyoxyethylene (8 mols) stearyl amine (designated "POE-SA", hereinafter) in the compounding ratio shown in the following table. The insecticide composition thus prepared was placed in an open vessel and stored at 40°C. After a fixed time, the sample was analyzed to determine the change in purity of the sample. The results obtained are shown in Table 5 below assuming the orignal purity of the sample was 100%.

TABLE 5

| Test Sample | Additive | POE-SA | Change in Purity of Insecticide III | | | |
|---|---|---|---|---|---|---|
| | | | Initial | 30 Days | 60 Days | 90 Days |
| Invention | A 2% | none | 100 | 96 | 95 | 92 |
| " | A 1% | 1% | 100 | 100 | 100 | 97 |
| " | B 2% | none | 100 | 96 | 93 | 88 |
| " | B 1% | 1% | 100 | 100 | 97 | 95 |
| Comparison Samples | C 2% | none | 100 | 85 | 63 | 48 |
| " | C 1% | 1% | 100 | 90 | 73 | 55 |

The results show that Additives A and B of this invention were quite effective in stabilizing Insecticide III as compared with conventional Additive C and also this effect was further improved by the addition of the POE-SA additive.

EXAMPLE 6

A mixture of 0.6 g of Insecticide IV, 0.06 g of Additive A, and 3.0 g of piperonyl butoxide was placed in an aerosol can equipped with a valve and then a mixed propellent gas of Freon 11 (Registered Trademark of E.I. duPont de Nemours & Co., Inc. for monofluorotrichloromethane) and Freon 12 (Registered Trademark of E.I. duPont de Nemours & Co., Inc. for difluorodichloromethane) in a 1:1 by volume mixing ratio was introduced in the can throught the valve orifice until the entire contents were 300 g to provide Aerosol Composition (a) of this invention.

Also, a mixture of 0.6 g of Insecticide IV, 0.06 g of Additive B, and 3.0 g of piperonyl butoxide was placed in an aerosol can and then the above-described procedure was repeated to produce Aerosol Composition (b) of this invention.

A mixture of 0.6 g of Insecticide IV, 0.06 g of Additive C, and 3.0 of piperonyl butoxide was placed in an aerosol can and the same procedure as described above was repeated to provide comparison Aerosol Composition C.

A filter paper having diameter of 20 cm was placed vertically and Aerosol Composition (a) prepared as described above was sprayed onto the filter paper in an amount of 10 g per filter paper. By repeating the same procedure, 12 filter papers were prepared and 9 filter papers of the 12 filter papers thus treated with the aerosol composition were hung on the wall of a room using pins.

The same procedure as described above was conducted for Aerosol Compositions (b) and (c) and the filter papers thus treated were also hung on the wall.

The three filter papers of the 12 filter papers thus treated with the aerosol composition were analyzed initially and the other 9 filter papers hung on the wall were analyzed after a fixed time in each case, whereby the amount of Insecticide IV remaining was determined in each case. The results obtained are shown in Table 6.

TABLE 6

| Test Sample | Composition | Change in Amount Remaining (mg per filter paper) | | | |
|---|---|---|---|---|---|
| | | Initial | 3 Days | 6 Days | 12 Days |
| Invention | (a) | 5.3 (100) | 4.1 (76.5) | 3.1 (58.5) | 2.2 (41.00) |
| " | (b) | 5.8 (100) | 4.5 (78.4) | 3.6 (62.0) | 2.6 (45.3) |
| Comparison Sample | (c) | 5.5 (100) | 3.1 (56.2) | 2.0 (35.5) | 0.9 (16.1) |

Note:
The figures in the parentheses are the percentage of the insecticide remaining assuming the initial amount to be 100%.

The above results show that in the case of treating using an aerosol composition, the effect of Additives A and B of this invention was quite remarkable as compared with the effect of conventional Additive C.

The aerosol compositions illustrated above are insecticidal compositions mainly used for the disinfection of the interior of aircraft but it will be readily understood that the effect of the additives of this invention will be obtained in aerosol insecticidal compositions used for domestic purposes.

While the invention has been described in detail and with reference to specific embodiments thereof, it will be apparent to one skilled in the art that various changes and modifications can be made therein without departing from the spirit and scope thereof.

What is claimed is:

1. A stabilized insecticidal composition comprising an insecticidally effective amount of a synthetic pyrethroidal insecticide and as a stabilizer at least one of a member selected from the group consisting of 3,5-di-t-butyl-hydroxyanisole and 2,2'-methylenebis(6-t-butyl-4-ethylphenol), wherein said synthetic pyrethroidal insecticide is chrysanthemum-mono-carboxylic acid 5-propargyl-2furyl methyl ester, chrysanthemum-monocarboxylic acid 2-methyl-5-propargyl-3-furyl methyl ester, chrysanthemum-monocarboxylic acid 5-propargyl-α-ethynyl-2-furyl methyl ester, chrysanthemum-monocarboxylic acid 5-benzyl-3-furyl methyl ester or 2,2-dimethyl-3-(2,2-dichlorovinyl)cyclopropane-1-carboxylic acid 5-benzyl-3-furyl methyl ester, and the proportion of said stabilizer is 0.05 to 3% by weight of the synthetic pyrethroidal insecticide.

2. An aerosol insecticidal composition comprising a propellant and an insecticidally effective amount of the composition of claim 1.

* * * * *